(12) United States Patent
Dave et al.

(10) Patent No.: US 7,799,536 B2
(45) Date of Patent: Sep. 21, 2010

(54) ENDOTHELIAL-MONOCYTE ACTIVATING POLYPEPTIDE II, A BIOMARKER FOR USE IN DIAGNOSIS OF BRAIN INJURY

(75) Inventors: Jitendra Ramanlal Dave, Gaithersburg, MD (US); Changping Yao, Gaithersburg, MD (US); Anthony Joseph Williams, Middletown, MD (US); Xi-Chun May, Laurel, MD (US); Frank Casper Tortella, Columbia, MD (US); Ka-Wang Kevin Wang, Gainsville, FL (US); Ronald Lawrence Hayes, Gainsville, FL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/290,174

(22) Filed: Oct. 28, 2008

(65) Prior Publication Data

US 2009/0068691 A1    Mar. 12, 2009

Related U.S. Application Data

(63) Continuation of application No. PCT/US2007/011613, filed on May 15, 2007.

(60) Provisional application No. 60/809,986, filed on May 18, 2006.

(51) Int. Cl.
*G01N 33/53* (2006.01)
*G01N 33/567* (2006.01)
*G01N 33/566* (2006.01)

(52) U.S. Cl. .................... 435/7.92; 435/7.21; 435/7.9; 436/501; 436/503

(58) Field of Classification Search .................. None
See application file for complete search history.

(56) References Cited

FOREIGN PATENT DOCUMENTS

WO    WO 2005/106038 A    11/2005

OTHER PUBLICATIONS

Mueller, et al., Lesional expression of a proinflammatory and antiangiogenic cytokine EMP II confined to endotheliam and microglia/macrophages during secondary damage following experimental traumatic brain injury., J Neuroimmunol., vol. 135, No. 1-2, Feb. 2003, pp. 1-9.
Brabeck, et al. Expression of EMAP II by activated monocytes, microglial cells in different regions of hte rat hippocampus after trimethyltin Induced brain damage., Exp Neurol., vol. 177, No. 1 Sep. 2002, pp. 341-346.
Shalak, et al., The EMAPII cytokine is reeased from the mammalian multisynthetase complex after cleavage of its p43/proEMAPII component., J Biol Chem, vol. 276, No. 26, Jun. 2001, pp. 23769-23776.
Lee, et al., Penetrating brain injury leads to activation of ciliary neurothrophic factor receptors, Neurosci Lett, vole 374, No. 3, Feb. 2005, pp. 161-165.
Choi, et al., Upregulation of gp130 and STAT 3 activation in the rat hippocampus following transient forebrain ischemia, GLIA, bol. 41, No. 3, Feb. 2003, pp. 237-246.
Gabbita, et al., Cleaved-tau, A biomarker of neuronal damage after traumatic brain injury, J Neurotrauma, vol. 22, No. 1, Jan. 2005, pp. 83-94.
Database Medline [Online] US National Library of Medicine, Bethesda, MD US, Nov. 2005, Siman et al., Novel surrogate markers for acute brain damage: cerebrospinal fluid levels correlate with seberity of ischemic neurodegeneration in the rat., XP002470879, Database accession No. NLM15902199, cited in the appl. abstract & J Cerebr Blood Flow Metabol, vol. 25, No. 11, Nov. 2005, pp. 1433-1444.

*Primary Examiner*—Olga N Chernyshev
(74) *Attorney, Agent, or Firm*—Elizabeth Arwine (57) ABSTRACT

A diagnostic tool and method of diagnosing brain injury and brain injury type (traumatic vs. ischemic) by detecting the level of expression of endothelial monocyte-activating polypeptide II (EMAP-II) and comparing to a control. An increase of EMAP-II indicates the presence of traumatic brain injury and a decrease of EMAP-II indicates the presence of ischemic brain injury. Detection of EMAP-II can be done in brain tissue, biofluids such as cerebrospinal fluid or blood (including plasma and serum).

3 Claims, 9 Drawing Sheets

ENDOTHELIAL-MONOCYTE ACTIVATING POLYPEPTIDE II, A BIOMARKER FOR USE IN DIAGNOSIS OF BRAIN INJURY

This application claims priority and is a continuation of PCT application serial number PCT/US2007/011613 filed 15 May 2007, pending, which claims priority of U.S. provisional application Ser. No. 60/809,986 filed 18 May 2006.

The invention described herein may be manufactured, used and licensed by or for the U.S. Government.

BACKGROUND OF THE INVENTION

1. Field of the Invention

The invention apprise to the use of a polypeptide, Endothelial-monocyte activating polypeptide II (EMAP-II) as a biomarker to determine the presence and type of brain injury.

2. Brief Description of Related Art

Traumatic brain injury is a leading cause of death and disability in the United States. One to 1.5 million Americans incurs a traumatic brain injury (TBI) each year. TBI is also a significant health problem for the uniformed services. Accurate diagnosis of brain-injury, severity and prognosis cannot be determined without skill and equipment typically located at an Echelon III facility (usually 1-8 hours after injury). Combat medics are not equipped with the requisite skills to accurately diagnose and triage brain-injured casualties. Therefore, a biomarker or biomarkers that can determine the severity and type of brain injury would be very useful both in combat and during sporting events.

Recent attention has focused on the development of protein biomarkers for the diagnosis and treatment of brain injury. Acute brain injury can induce a variety of signaling cascades, involving changes in post-translational protein modifications and expression of multiple genes that can lead to secondary injury (Lu et al., 2004). Differentiation of the pathological mechanisms underlying traumatic and ischemic brain injuries has been difficult due to the involvement of overlapping cellular and molecular pathways, presenting a great challenge for developing injury-specific therapeutics or management protocols. As such, improvements in methodology for the diagnosis/prognosis of the brain-injured patient can be of immense therapeutic value to define optimal neuroprotection strategies.

Two main categories of experimental models used to study brain injury are those due to a predominately ischemic-type injury (i.e., arterial occlusion models) or traumatic-induced injury (i.e. fluid percussion, cortical impact, cortical stab or penetrating missile wound models). Using these models, post-injury expression of numerous proteins have been independently identified and reported. Many cytoskeletal components, transcription factors, programmed cell death proteins, and protein kinase regulators are expressed predominantly in neurons, and are candidate biomarkers for selective detection of brain damage (Ingebrigsten and Romner, 2002). These proteins become accessible in body fluids following brain injury and associated blood-brain-barrier (BBB) disruption permitting minimally-invasive quantification, an essential characterization for their use as diagnostic and prognostic markers of brain injury. Consequently, increasing efforts have been devoted to the development of high-throughput differential techniques for detection of injury-mediated changes in proteins.

To date, several proteins have been studied as potential biomarkers including creatine kinase, glial fibrillary acidic protein, lactate dehydrogenase, myelin basic protein, neuron-specific enolase, S-100 protein, as well as others (Ingebrigtsen and Romner, 2002); however, all of these proteins have been ineffective as stand-alone markers of brain injury (Kobeissy et al., 2006). In response, recent efforts have been aimed at the development of a panel of biomarkers including not only surrogate markers related to injury outcome (Ingebrigtsen and Romner, 2002) but also markers providing specific information about the molecular mechanism of injury (i.e., true biochemical markers) (Liu et al., 2006a&b).

In previous studies, we characterized brain-injury changes in rat gene expression using real-time PCR and microarray techniques (Berti et al., 2002; Yao et al., 2002; Lu et al., 2004) and demonstrated the relevance of such data by using therapies specifically targeting aberrant gene transcription (Williams et al., 2004). However, PCR and microarray techniques focus on changes in gene expression at the mRNA level and do not necessarily reflect protein changes, for example due to degradation of transcriptional machinery in injured cells.

What is needed is a biomarker protein that is present in brain injury. What is also needed is a biomarker protein that is differentially regulated based on the type of brain injury. The biomarker needed could differentiate between an ischemic injury or traumatic injury.

These needs have become the objects of the present invention. The inventors observed changes in 30 out of 998 proteins following acute focal injuries to the brain. They found that one protein, EMAP-II was differentially expressed between two types of brain injury (traumatic vs. ischemic). EMAP-II is known to be an inflammatory cytokine involved in apoptotic processes. It was found that EMAP-II in brain and CSF are significantly increased 1.6-1.8 fold following penetrating ballistic brain injury but decreased 2.1-2.3 fold after ischemic injury compared to uninjured animals. The differential expression of EMAP-II is useful for diagnosis of traumatic vs. ischemic brain injury and provides valuable information for directing injury-specific therapeutics. Additionally, the inventors have found that EMAP-II levels were elevated in CSF in human patient suffering from traumatic brain injury, when compared to uninjured controls.

SUMMARY OF THE INVENTION

The present invention is directed to a diagnostic tool and method of diagnosing brain injury and brain injury type (traumatic vs. ischemic) by detecting the level of expression of endothelial monocyte-activating polypeptide II (EMAP-II) as compared to control levels. Elevated post-injury levels of EMAP-II indicate the presence of a penetrating/traumatic type brain injury. In contrast, a decrease in EMAP-II protein level would indicate the presence of a primarily ischemic type of brain injury.

DETAILED DESCRIPTION

In the current study, the inventors applied high-throughput immunoblotting technology (HTPI; BD PowerBlot™) (Liu et al., 2006a) to study large scale differential protein patterns in rat brains 24 hours after either a penetrating ballistic-like brain injury (PBBI) (Williams et al, 2005; Williams et al. 2006a; Williams et al. 2006b) or middle cerebral artery occlusion (MCAo) (Tortella et al., 1999). Specifically, the inventors focused on identifying proteins with measurable changes in protein abundance following acute brain injury. They further hypothesized that a subset of those proteins would cross the BBB to be detected in blood. The value of this approach was demonstrated when five proteins (STAT3, Tau, $PKA_{RII\beta}$, 14-3-3H and p43/EMAP-II), identified by our HTPI assay, were immunodetected as proteins released differentially into blood of PBBI or MCAo injured rats. It was found that the p43/EMAP-II candidate biomarker proved highly sensitive to detecting and distinguishing types and severities of brain injury and the underlying pathological processes, thereby advancing clinical diagnostics for evaluation of acute brain injury and patient monitoring.

EMAP-II is an inflammatory cytokine. Its proEMAP-II precursor is identical to the auxiliary p43 component of the aminoacyl-tRNA synthetase complex. EMAP-II domain of p43 is released readily from the complex after in vitro digestion with caspase 7 and is able to induce migration of human mononuclear phagocytes. P43 compares well with a molecular fuse that triggers the irreversible cell growth/cell death transition induced under apoptotic conditions. EMAP cytokine is released from the mammalian multisynthetase complex after cleavage of its p43/proEMAP-II component.

Materials and Methods

Adult male Sprague-Dawley rats (250-300 g; Charles River Labs, Raleigh, Va.) were used for all studies. Anesthesia was induced during all surgical manipulations by 5% isoflurane, and maintained at 2% isoflurane delivered in oxygen. All procedures were approved by the Walter Reed Army Institute of Research Animal Care and Use Committee. Research was conducted in compliance with the US Animal Welfare Act, *Guide for the Care and Use of Laboratory Animals* (National Research Council) and other federal statutes and regulations relating to animals and experiments involving animals. Animals were housed individually under a 12 hour light/dark cycle in a facility accredited by the Association for Assessment and Accreditation of Laboratory Animal Care International.

Middle Cerebral Artery Occlusion (MCAo) Model (Ischemic Injury)

Figure 9:
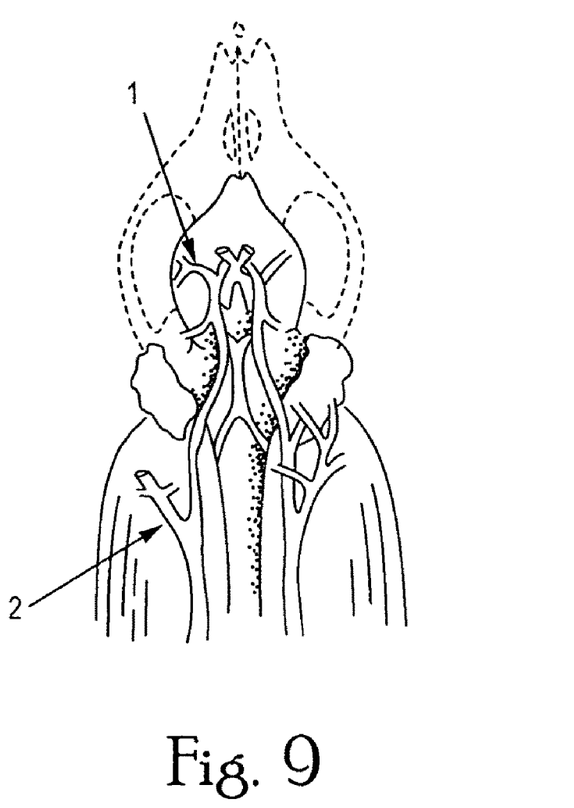
FIG. 9 is a conceptual drawing of a rat brain showing MCAo procedure.

Transient MCAo was carried out using the intraluminal filament model as described previously (Tortella et al., 1999). Briefly, the right external carotid artery was exposed, and its branches were coagulated. As shown in FIG. 9, a 3-0 uncoated monofilament nylon suture with rounded tip was inserted into the external carotid artery ECA, 2 and advanced until it lodged in the proximal region of the anterior cerebral artery, thus occluding the origin of the MCA, 1. The endovascular suture remained in place for 2 hours and was then retracted to allow reperfusion of blood to the middle cerebral artery (MCA). Sham (control) animals underwent the same surgical procedure but without the introduction of the filament into the MCA.

Penetrating Ballistic-Like Brain Injury (PBBI) Model

Figure 10:
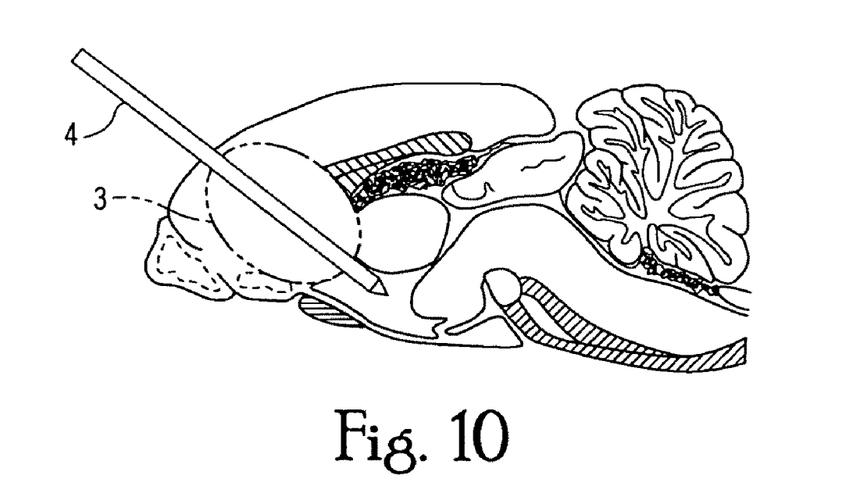
FIG. 10 is a conceptual drawing of a rat brain showing PBBI procedure.

PBBI was produced by insertion of a specially designed probe, which connected to the Dragonfly Variable Pressure Waveform Generator (model HPD-1700; Dragonfly Inc., W.Va.) to induce a rapid pressure pulse for expansion/contraction of the balloon inside the right hemisphere of brain (Moshang et al., 2003; Williams et al., 2005; Williams et al., 2006a; Williams et al., 2006b). Briefly, the balloon inflation device was constructed from a 20-gauge stainless steel tube with spatially fixed perforations at one end that were sealed by an airtight section of elastic tubing (PBBI balloon). The perforations are arranged in a pattern such that an air pulse delivered to an air cylinder will inflate the balloon in an elliptical shape. A "T" type junction, high-pressure manifold allows transmission of the pressure wave from the pressurizing piston and cylinder to both the implanted PBBI probe and the pressure transducer simultaneously. The induced pressure wave was measured directly by a precisely calibrated pressure transducer through a charge amplifier/coupler to a digital oscilloscope. The PBBI balloon does not expand until the pressure cylinder reaches near peak pressure with an average 'open' time of less than 10 ms as estimated by videotaping the balloon expansion event. Sham (control) animals underwent craniectomy without insertion of the PBBI probe. The rapid inflation and deflation of the balloon simulated a ballistic pressure wave causing a temporary intracranial cavity. Sham animals underwent craniotomy alone without insertion of the PBBI probe. In FIG. 10, the probe 4 and balloon expansion 3 are shown.

Brain Tissue Collection

Brain tissue was collected 24 hours following injury. Four experimental groups were assessed: PBBI, PBBI-sham, MCAo, and MCAo-sham. All animals were deeply anesthetized with ketamine/xylaxine (70 and 6 mg/kg, i.p., respectively) 24 hours post-injury. Brain tissue sections (2-3 mm thick) were dissected from the core lesion area (including frontal cortex and striatal brain regions) of each animal for Western Blot or HTPI analysis.

1. CSF (Cerebral Spinal Fluid)

The midline incision in the occipital region was made from 0.5 cm anterior to interauricular line of 4 cm in length. Exposing the atlanto-occipital dura mater by separating the nuchal muscles, the CSF was collected through a small hole made by an 18 G syringe needle. Usually 0.05-0.10 ml of the CSF could be obtained, if the injured brain was not significantly swollen. CSF samples were centrifuged at 2000 rpm at 4° C. for 10 min. The supernatant was collected into 1.5 ml tube and then stored in −80° C. for Western Blot and proteomics analysis.

2. Brain Tissue

A 3-mm coronal section of brain tissue was dissected out from each rat brain (to include cortical and striatal tissue) starting at 5 mm posterior to the frontal pole. Immediately, the brain tissues were separated from ipsilateral (injured) and contralateral (uninjured) hemispheres and then stored in −80° C. for HTPI, proteomics and Western blot analysis.

High-Throughput Immunoblotting

The HTPI procedure was performed on injured brain tissue as a custom service by BD Biosciences Transduction Laboratories (Bringamham, Ky.). Briefly, placed 200 mg pooled protein in 5 ml lysis buffer (10 mM Tris pH 7.4, 1 mM Sodium Orth-vanadate and, 1% SDS) on ice for 30 minutes, then sonicated and centrifuged at 3000 pm 4° C. for 15 minutes. Added 2× sample buffer (25 mM Tris pH 6.8, 4% SDS, 10% Glycerol, 0.006% Bromphenol Blue, 2% b-mercaptoethanol) in to the samples and then loaded the samples into a 13×10 cm, 0.5 mm thick, 4-15% gradient SDS-polyacrylamide gel (Bio-Rad Criterion IPG well comb) and run for 1.5 hours at 150 volts. The protein samples were then transferred to Immobilon-P membrane for 2 hours at 200 mA. After transfer, the membrane was dried, re-wetted in methanol and blocked for one hour with blocking buffer. The membrane was next clamped in a Western blotting manifold to isolate the 40 channels. A complex antibody cocktail was added to each channel and allowed to hybridize for one hour at 37° C. The blot was removed from the manifold, washed and hybridized for 30 min at 37° C. with secondary goat anti-mouse conjugated to Alexa 680 fluorescent dye. Fluorescence detection was performed at a wavelength of 700 nm using an Odyssey infrared imaging system.

Each experimental group consisted of two pooled samples and was run in triplicate using a 3×3 matrix comparison of each of the five HTPI templates (A-E). The HTPI templates included 39 lanes with 4-7 monoclonal antibodies probed in each. A 40$^{th}$ lane was probed with molecular weight marker-antibodies. Raw and normalized signal intensity of HTPI data was performed for each blot using BD Biosciences proprietary software. In total, each sample group was probed with 998 well-characterized monoclonal antibodies to produce a protein profile of injured to non-injured brain for comparison of PBBI and MCAo injuries. Data is reported as a fold-change increase or decrease between sham and injured samples for each injury type.

Western Blotting

Western blotting was performed on brain lysate and CSF samples (n=3-6 per group) as described previously (Chen et al., 1999) with individual protein antibodies taken from the HTPI panel. 100 ul of plasma with 200 ul lyses buffer or 100 mg brain tissue with 500 ul lyses buffer (20 mM Tris, pH 7.4, 150 mM NaCl, 5 mM EDTA, 5 mM EGTA, 1% TritonX-100 and 1 mM DTT and 1× Protease inhibitor) were well mixed on ice for 30 mins, then sonicated 10 to 20 seconds. Protein lysate were centrifuged at 3000 rpm at 4° C. for 15 mins. Concentrations of the proteins in the preparations were determined using the BCA™ Protein Assay Kit (PIERCE, Rockford, Ill.). Twenty micrograms of each sample were loaded and separated by 4-20% SDS-polyacrylamide gradient gel electrophoresis and then transferred to an Immobilon-P membrane (Chen et al., 2003). After blocking for one hour in PBST (10 mM sodium phosphate, 0.9% NaCl and 0.1% Tween 20) containing 5% nonfat dry milk, blots were incubated overnight at 4° C. with the primary antibodies STAT3 (Cat# 610189), Tau (Cat# 610672), PKA$_{RIIβ}$ (Cat# 610625), 14-3-3H (Cat#610542), p43/EMAP-II precursor (Cat# 611884) (BD Bioscience Pharmingen, CA), respectively, in PBST containing 3% nonfat milk. Blots were washed four times in PBST (40 min) and incubated for one hour with horseradish peroxidase-conjugated secondary antibody in PBST containing 3% nonfat dry milk. Immunoreactivities of the protein bands were detected by enhanced chemiluminescent autoradiography (ECL kit, Amersham Pharmacia Biotech, Piscataway, N.J.) as instructed by the manufacturer. A molecular weight standard (Bio-Rad Laboratories, Hercules, Calif.) was loaded in the last lane of each gel to assess relative molecular mass of detected bands.

Immunohistochemistry

Upon removal from the skull, rat brains were rapidly frozen in −70° C. isopentane pre-cooled with dry ice. Two cryostat sections (20 μm) were cut coronally through the cerebral cortex containing the striatum (approximately 5 mm from the frontal pole cf. the Rat Brain in Stereotaxic Coordinates by Paxinos & Watson, 1986). Every first and second section of each rat brain was mounted directly on Superfrost plus slides. The sections of the first set were stained with hematoxylin & eosin. The sections of the second set were processed for p43/EMAP-II-immunohistochemistry. Thus, sections were fixed in 0.1M phosphate buffer (pH 7.4) containing 4% paraformaldehyde for 30 minutes at 4° C., followed by washes in 0.01 M phosphate-buffered saline (PBS; pH 7.4). After inactivating the endogenous peroxidase activity with hydrogen peroxidase, sections were incubated separately with avidin and biotin solutions (Vector Lab, Burlingame, Calif.) for blocking nonspecific binding of endogenouse biotin, biotin-binding protein and lectins. Sections were then incubated for overnight at 4° C. in 0.01 M PBS containing 1% normal goat serum, 4% BSA, 0.1% Triton X-100 (Sigma, St. Louis, Mo.) and a mouse monoclonal EMAP-II precursor antibody (BD Bioscience Pharmingen, CA). Subsequently, the immunoreaction product will be visualized according to the avidin-biotin complex method of Hsu et al. (1981) with the Vectastin elite ABC Peroxidase kit (Vector Lab., Burlingame, Calif.).). Briefly, sections were incubated in the PBS with Triton-X and normal goat serum containing biotinylated goat anti-rabbit IgG for 1 hour and then in the PBS solution containing avidin-biotinylated horseradish peroxidase complex for another hour. This was followed by incubation of the sections for 10 minutes in 0.05 M Tris buffer (pH 7.2) containing 0.03% 3',3'-diaminobenzidine (Sigma) and 0.0075% $H_2O_2$. All steps were carried out at room temperature, and each step was followed by washes in PBS. After thorough rinses in distilled water, sections were mounted on slides, dehydrated in ethanol, cleared in xylene, and coverslipped in Permount® (Fisher Scientific, Fair Lawn, N.J.).

ELISA Assay

EMAP-II sandwich ELISA (from Biosource International, Invitrogen Corporation, Carlsbad, Calif.) was performed according to manufacturer's instructions. Individual or pooled human CSF (20 μL) and serum (50 μL) were used for analysis.

Statistic Analysis

Western blot: Densitometric quantification of the immunoblot bands was performed using Scion Image (NIH, Bethesda, Md.). Measurements are presented as mean values±standard error of the mean (S.E.M.). Statistical comparisons were done by analysis of variance (ANOVA) followed by post-hoc t-test analysis of evaluation between groups. Values were considered to be significant at $p<0.05$.

Results

Brain Injury

Figure 1:
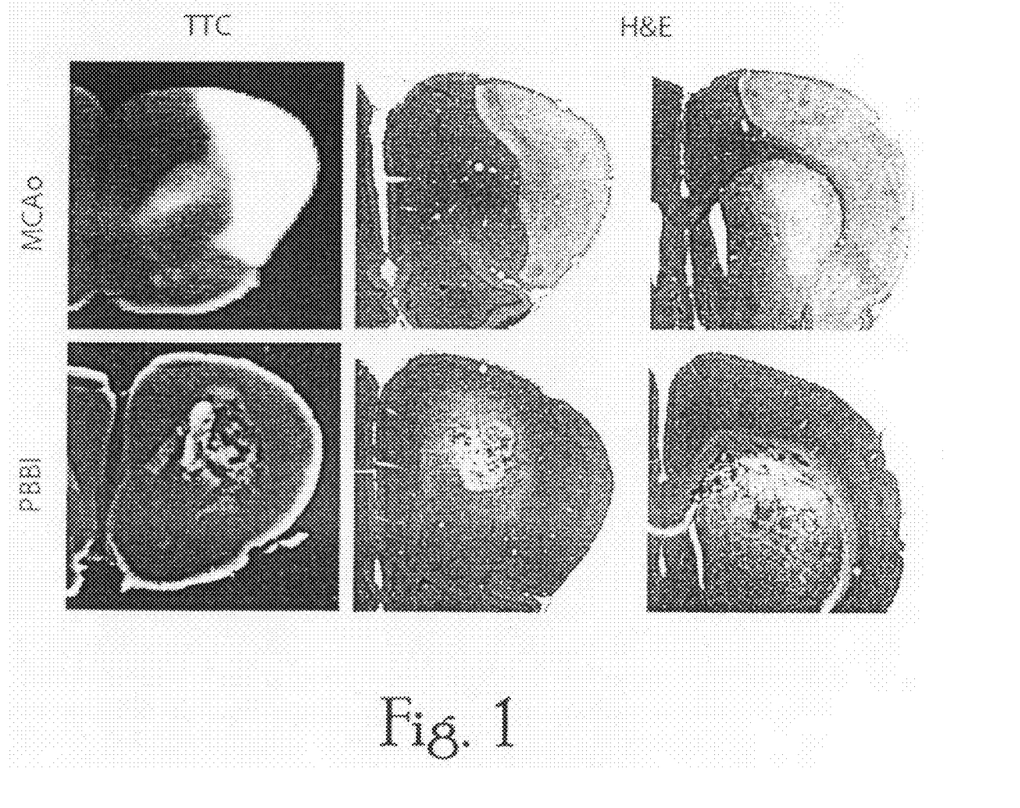
FIG. 1 is a series of coronal sections of rat brains 24 hours following PBBI or MCAo injury.

Both MCAo and PBBI resulted in brain lesions throughout the right frontal cortex and striatum (FIG. 1). MCAo induced a non-hemorrhagic lesion typically involving a large volume of infarcted tissue as indicated by TTC staining, while the PBBI lesion was seen as tissue damage with a distinct hemorrhagic component as indicated by red blood cell infiltration.

High-Throughput Immunoblotting

HTPI analysis was used to detect differential protein changes in brain tissues of injured animals. Twenty-nine out of 998 screened proteins had an abundance difference of 1.5-fold or greater following either PBBI or MCAo (Table 1). Compared to matching sham control samples (FIG. 2b), 18 proteins (8 increased and 10 decreased) from the PBBI model (FIG. 2a) and 17 proteins (8 increased and 9 decreased) from the MCAo model (FIG. 3a) showed an altered abundance. Of those proteins, 79.3% ($^{23}/_{29}$) were differential in only one model, 17.2% ($^5/_{29}$) had similarly changed in both models, while only one protein, p43/EMAP-II, (3.4%) showed an opposite change between the two models (Table 1 & FIGS. 4a-4c).

Western Blotting

Figure 5A:
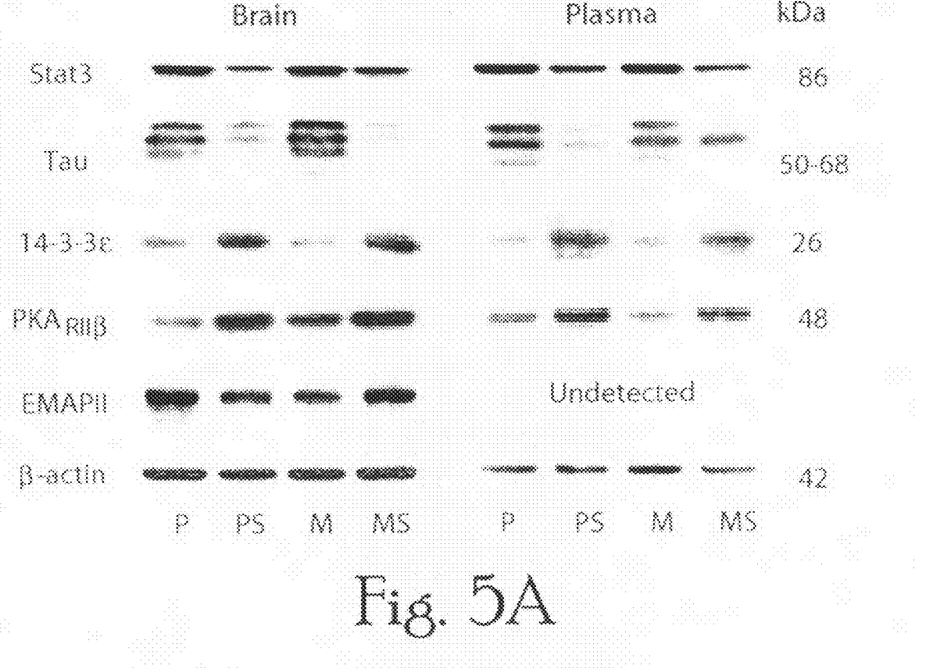
FIG. 5a is a digital image showing Western Blot analysis (WB) of changes for selected proteins in both blood (plasma) and brain.
Figure 5B:
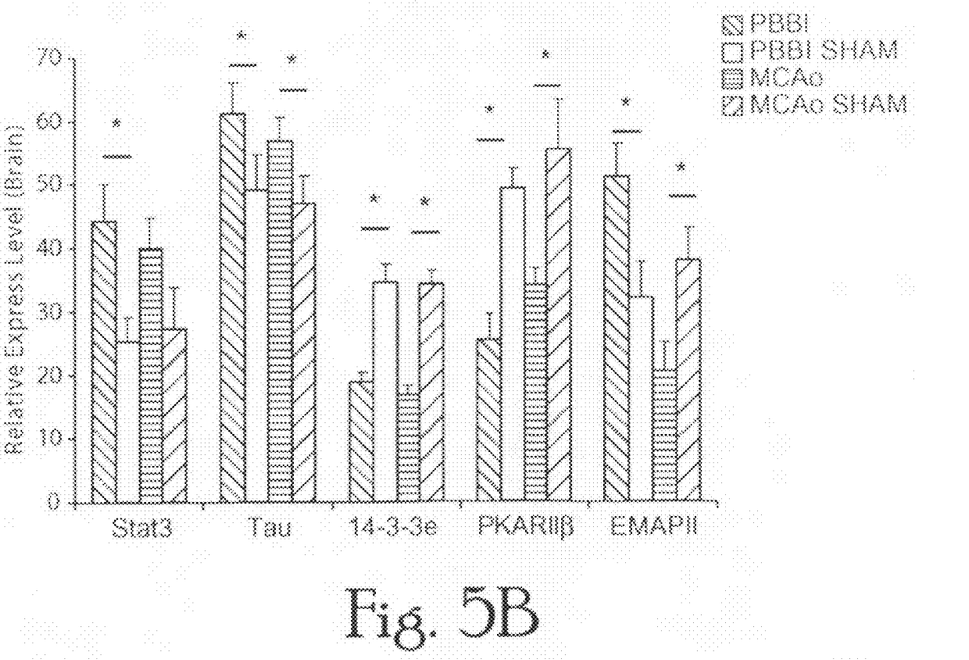
FIG. 5b is a graph showing quantitative measurement of WB density in brain tissues.

Thirteen of 29 proteins with altered abundance were verified by Western Blot analysis using individual protein antibodies taken from the HTPI panel. Eight of the antibodies (Fas antigen ligand, minichromosome maintenance protein 2 homolog (BM28), collybistin, F-actin binding protein b-Nexilin, dopamine- and cAMP-regulated neuronal phosphoprotein, microtubule-associated protein 2B (MAP2B), and MKK7) indicated low-reactivity in the band of interest or poor resolution in blood or brain samples (data not shown). In contrast, protein levels of STAT3, Tau, $PKA_{RII\beta}$, 14-3-3H and p43/EMAP-II all indicated high resolution and good reactivity in both blood and brain (FIGS. 5a and 5b). Western blot data also confirmed that STAT3 and Tau increased in both injury models, while $PKA_{RII\beta}$ and 14-3-3H decreased in both models (Table 2). p43/EMAP-II was also confirmed to change oppositely in abundance following PBBI (increased) and MCAo (decreased) in both blood and brain samples (FIGS. 5a and 5b). P=PBBI, PS=PBBI Sham, M=MCAo, MS=MCAo Sham.

ELISA

Using sandwich ELISA specific to human EMAP-II, it was found that EMAP-II levels were elevated in CSF and serum at different time points in a human patient suffering from traumatic brain injury, when compared to uninjured controls (Table 3). In addition, EMAP-II levels in pooled CSF and serum samples from traumatic brain injury patients at some time points were also elevated when compared to those in pooled uninjured controls.

DISCUSSION

In the current study HTPI technology was used to compare the altered abundance of 998 proteins following PBBI or MCAo injuries to the rat brain. Twenty-nine proteins were found to be altered in abundance post-injury, of which five proteins were validated using Western Blots from both blood and brain samples (i.e. STAT3, Tau, $PKA_{RII}$, 14-3-3H and p43/EMAP-II).

The most interesting of the identified proteins was endothelial monocyte-activating polypeptide II (EMAP-II), which was found to increase in one injury paradigm (PBBI) and decrease in the other (MCAo). EMAP-II has been described as an inflammatory cytokine that stimulates the chemotactic migration of inflammatory cells, and also induces the expression of endothelial tissue factors necessary for coagulation (Behrendsdorf et al., 2000). Increased expression of EMAP-II has been reported in endothelial cells and microglia/macrophages following a stab wound to the rat brain (Mueller et al., 2003) or hemisection lesion of the rat spinal cord (Mueller et al., 2003). Interestingly, EMAP-II is synthesized from the precursor protein p43/EMAP-II that lacks a secretion signal peptide (Quevillon et al., 1997). EMAP-II is released from apoptotic cells following cleavage by the pro-apoptotic enzymes caspase-3 and -7 (Behrendsdorf et al., 2000), and may be an important molecule linking apoptosis and inflammation (Daemen et al., 1999).

Importantly, p43/EMAP-II was the only protein that had an opposite abundance change between the two injury models, potentially allowing distinction between hemorrhagic and non-hemorrhagic injuries. The increase of p43/EMAP-II following PBBI could reflect a pro-coagulatory response to the marked intracranial hemorrhaging inherent to PBBI and absent in the MCAo model (Williams et al., 2006a).

Signal transducer and activator of transcription 3 (STAT3), a cytoplasmic signal transduction and transcription activator protein, was found elevated in blood samples of both MCAo and PBBI injured rats. STAT3 has been identified as a key component linking cytokine signals with transcriptional events. STAT3 also participates in biological processes such as cell-cycle progression, apoptosis, tumor angiogenesis, tumor-cell invasion, and metastasis (Mechoulam et al., 2005; Lee and Pearce, 2005). In fact, STAT proteins have been linked with neuroprotection against ischemia/reperfusion (I/R) injury after ischemic preconditioning, and function as modulators of cytokine signaling and sensors responding to cellular ischemia (Li and Zhang, 2003; Choi et al., 2003).

Tau is a microtubular binding protein localized in the axon of neurons that plays a fundamental role in the intracellular microtubule dynamics of brain cells (Irazuzta et al., 2001; Siman et al., 2005). Previous reports have indicated that brain Tau levels are associated with TBI-induced tissue loss, and that Tau levels in blood can indicate severity of TBI-induced brain injury (Gabbita et al., 2005). Increased blood and brain levels of Tau have also been detected after ischemic stroke (Funahashi et al., 2003). Similarly, the current study verified the increase in Tau protein following both PBBI and MCAo injuries.

Blood levels of the RIIβ regulatory subunit of protein kinase A ($PKA_{RII\beta}$) and 14-3-3H protein were both decreased following PBBI or MCAo injuries. $PKA_{RII\beta}$ is involved in a variety of cAMP-mediated cellular processes related to cell growth and differentiation (Budillon et al., 1995; Li et al., 1995). 14-3-3H is a member of the family of well-conserved chaperone proteins originally isolated from mammalian brain preparations and known to possess diverse biochemical activities related to signal transduction (Conklin et al., 1995) including regulation of apoptosis (Saito et al., 2004; Tsuruta et al., 2004). The decrease of $PKA_{RII\beta}$ and 14-3-3H at the protein level may reflect cellular deterioration or intracellular signaling dysfunction induced by brain injury.

Our results indicate that HTPI is sensitive to changes in protein levels following acute injury to the brain and provide a differential profile of ischemic versus ballistic type injuries. These studies demonstrate the utility of HTPI for rapid characterization of the altered neuroproteome following brain injury. However, further evaluation of the identified proteins must be undertaken, particularly in minimally-invasive biofluids such as blood (Hu et al., 2006), before a true biomarker can be developed into a clinical diagnostic. Additional work will be necessary to evaluate time course profiles in protein expression, assess brain specificity, and compare to functional outcome or mechanism of injury. Ideally, changes in blood protein levels will be useful in tracking brain injury severity and degree of recovery (Ingebrigsten and Romner, 2002). Future research is underway in our laboratory to meet these mounting goals.

In conclusion, we have demonstrated that HTPI analysis provides a comprehensive protein screening tool to facilitate the differential profiling of acute brain injuries. Several candidate biomarkers were identified that were either increased (STAT3 & Tau), decreased (14-3-3ε protein & $PKA_{RIIE}$), or differentially altered (p43/EMAP-II) in abundance following PBBI and MCAo injuries. Further, these markers were validated and verified in rat CSF to be differentially detectable following both injuries. Lastly, it was also found that EMAP-II levels were elevated in CSF in human patient suffering from traumatic brain injury, when compared to uninjured controls. We have confirmed that these protein changes can track with the injury type.

Other protein detection methods that are suitable are protein chip, Western Blotting and ELISA.

The measurement of EMAP-II has applications in human and veterinary medicine. The human sequence of EMAP-II is well known. Shalak, et al. J. Biol Chem 2001 Jun. 29; 276 (26):23769-76. Epub 2001 Apr. 16. EMAP is processes by caspase to mature form (EMAP-II). This invention covers EMAP-II in full length and in processed form. The protein accession number for EMAP-II is Q12904 (DNA accession number NM_004757). Our tests show that the same result is achieved in rat and mouse EMAP-II, Gene Bank (PubMed-indexed for MEDLINE) sequence accession numbers NP_446209 XP_342345 (rat) and NP_031952 (mouse).

The data of the invention is useful as a diagnostic tool that is essentially a differential profile containing levels of EMAP-II and/or p43/EMAP-II, STAT3, Tau 14-3-3ε protein, and $PKA_{RIIE}$ from one or more patients that have suffered brain injury, and one or more control patients. By comparing the differential profile of these proteins from a brain injury patient with a control, it can be determined whether a patient has suffered brain injury and whether the injury is traumatic or ischemic. The differential profiles may be contained on a protein chip or multiplexed ELISA.

Further, EMAP-II has utilities in detecting any form of brain injury, e.g. induced by chemical toxins, poisons (including psycho stimulants methamphetamine, ecstasy), nerve gas, brain injury induced by seizure and neurodegeneration (Alzheimer's disease, Parkinson's and ALS).

TABLE 1

Protein level changes after PBBI or MCAo as identified by HTPI.[1]

| | Protein Name | SwissProID | MW (kDa) | PBBI vs sham (fold change) | MCAo vs sham (fold change) |
|---|---|---|---|---|---|
| | Adaptors & Tyrosine Kinase Substrates | | | | |
| 1 | c-Jun N-terminal kinase (JNK)-interacting protein 1 (JIP-1), | Q9WV1 | 112 | NC | div/0 |
| 2 | Cytoplasmic protein NCK1 | P16333 | 44 | NC | −1.95 |
| 3 | Neurotensin Receptor 3 | Q99523 | 107 | NC | −1.93 |
| 4 | Nuclear protein BM28 | Q9Z1Z2 | 39 | 1.55 | NC |
| | Apoptosis | | | | |
| 5 | P43/Endothelial monocyte-activating polypeptide 2 (p43/EMAP-II) | P31230 | 37 | 2.81 | −2.33 |
| 6 | Fas antigen ligand | P48023 | 32 | −1.68 | NC |
| | Cell cycle and cell proliferation | | | | |
| 7 | General vesicular transport factor p115 | P41542 | 106 | NC | 1.87 |
| 8 | Protein farnesyltransferase subunit beta | P49356 | 44 | NC | −1.68 |
| 9 | Protein phosphatase 2C isoform delta | Q9QZ67 | 55 | 1.67 | 2.24 |
| 10 | Retinal-cadherin | Q63149 | 98 | NC | 2.46 |
| | Cytoskeleton | | | | |
| 11 | F-actin binding protein b-Nexilin | Q9Z2J4 | 95 | −2.41 | NC |
| 12 | Microtubule-associated protein (MAP2B) | P11137 | 280 | 2.56 | NC |
| 13 | Microtubule-associated protein tau | P10636 | 66 | 3.62 | NC |
| | Ion channel | | | | |
| 14 | Neuronal calcium sensor (NCS-1) | P36610 | 19 | NC | −3.3 |
| 15 | Na+, K+ ATPase b2 | Q5M9H4 | 41 | NC | −2.65 |
| | Nucleus & Nuclear Transport | | | | |
| 16 | Minichromosome maintenance protein 2 homolog (BM28) | P49736 | 129 | 3.25 | NC |
| 17 | Nuclear transport factor 2 | P13662 | 20 | −4.19 | −2.17 |
| 18 | Retinoblastoma-binding protein (Bog) | O88350 | 20 | NC | 3.13 |
| 19 | Karyopherin a/Rch-1 | P52292 | 60 | −2.35 | NC |
| | Signal transduction | | | | |
| 20 | 14-3-3 protein epsilon | P42655 | 26 | −2.69 | NC |
| 21 | cAMP-dependent protein kinase type II-beta regulatory subunit (PKARIIβ) | P12369 | 48 | −2.06 | −2.25 |
| 22 | Collybistin | Q9QX73 | 117 | NC | 3.99 |
| 23 | MKK7 | O35406 | 59 | −1.58 | NC |
| | Transcription factor | | | | |
| 24 | Period circadian protein 2 | Q9Z301 | 104 | −2.32 | NC |
| 25 | Signal transducer and activator of transcription 3 (STAT3) | P52631 | 86 | 5.52 | div/0 |
| | Others | | | | |
| 26 | Tyrosine 3-monooxygenase | P04177 | 95 | −2.1 | NC |
| 27 | Dopamine- and cAMP-regulated neuronal phosphoprotein (DARPP) | Q9UD71 | 32 | NC | −9.81 |

TABLE 1-continued

Protein level changes after PBBI or MCAo as identified by HTPI.[1]

| Protein Name | SwissProID | MW (kDa) | PBBI vs sham (fold change) | MCAo vs sham (fold change) |
|---|---|---|---|---|
| 28 Acetylcholinesterase | P22303 | 75 | −2.68 | NC |
| 29 Syntaxin 6 | Q63635 | 31 | 2.14 | 1.97 |

[1]Protein level changes (±1.5 fold change from sham) after PBBI or MCAo (24 hours) as identified by HTPI. "NC" indicates no change or change less than 1.5 fold, "div/0" represents presence verses absence of a protein (i.e. fold change is increased but immeasurable). MW is observed molecular weight. Results collected across 5 protein templates.

TABLE 2

Comparison of HTPI and Western Blot data from brain.[1]

| | HTPI | | Western Blotting | |
|---|---|---|---|---|
| Protein | PBBI/sham | MCAo/sham | PBBI/sham | MCAo/sham |
| STAT3 | + | + | + | + |
| Tau | + | NC | + | + |
| PKA$_{RIIE}$ | − | − | − | − |
| 14-3-3H | − | NC | − | − |
| p43/EMAP-II | + | − | + | − |

[1]Comparison of HTPI and Western Blot data from brain. (+ or − change as compared to sham). NC represents no change or change less than 1.5 fold.

FIG. 1: Representative coronal sections of rat brains 24 hours following PBBI or MCAo injury. Infarction is indicated by the bright white regions of TTC staining or neuropil pallor in H&E slides. Regions with intracranial hemorrhage are denoted by bright red regions (H&E) throughout the core lesion of PBBI injured rats.

Figure 2A:
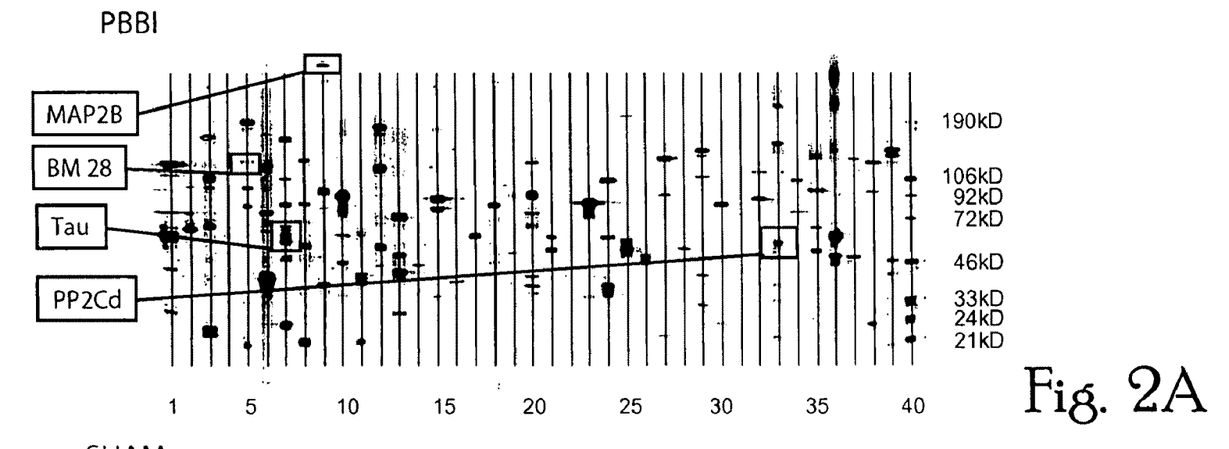
FIG. 2a is a power blot template of PBBI (A) brain tissue 24 hours post-injury.
Figure 2B:
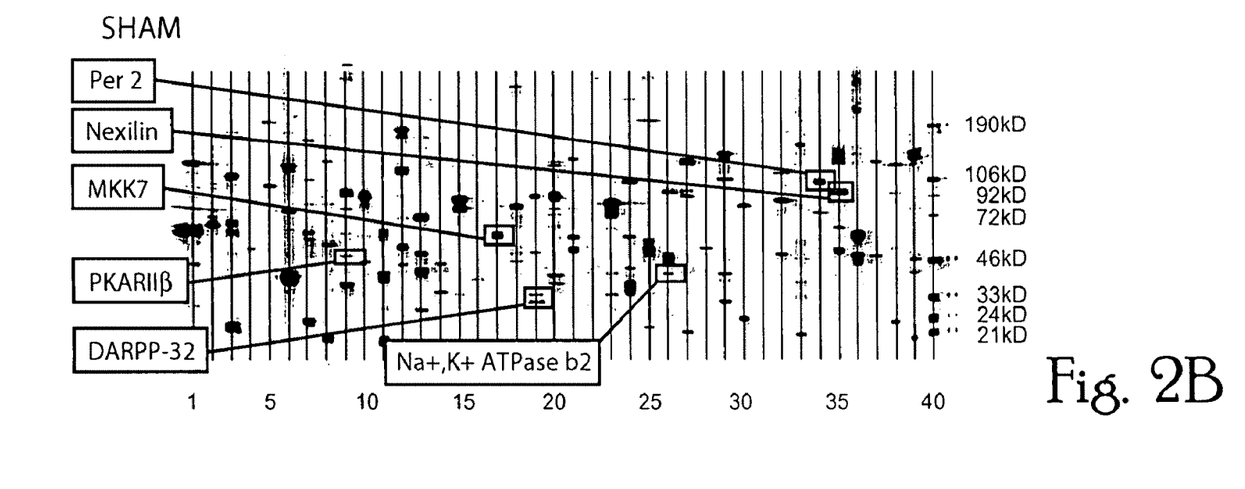
FIG. 2b is a power blot template of the sham (B) brain tissue 24 hours post-injury.

FIGS. 2a and 2b: Representative power blot templates of PBBI (A) and sham (B) brain tissue 24 hours post-injury. Each template consisted of 39 lanes of 4-7 antibody probes each. The far right lane contains molecular weight markers for reference. The named protein spots were either increased or decreased relative to sham animals.

Figure 3A:
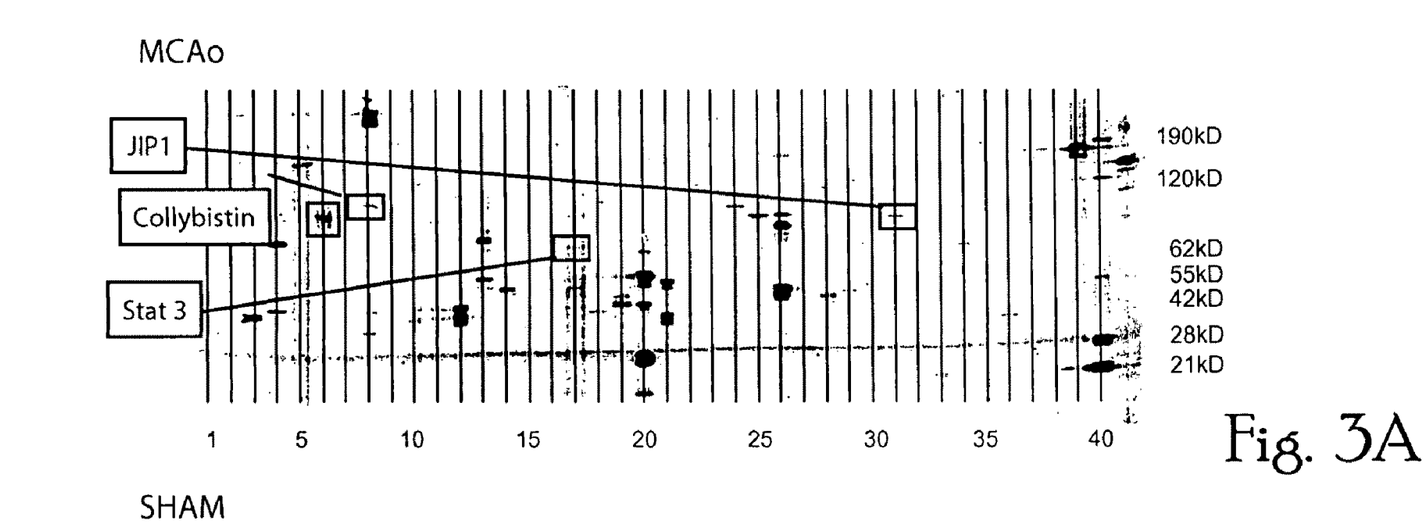
FIG. 3a is a power blot template of MCAo (A) brain tissue 24 hours post-injury.
Figure 3B:
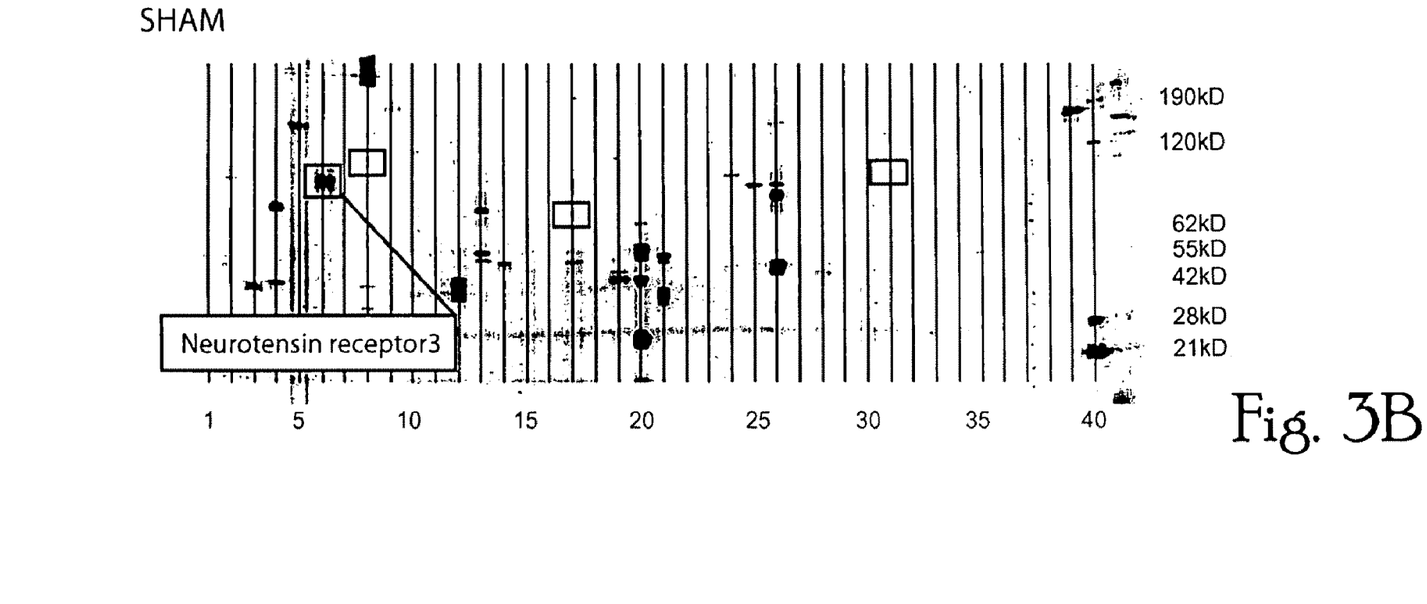
FIG. 3b is a power blot template of the sham (B) brain tissue 24 hours post-injury.

FIGS. 3a and 3b: Representative power blot templates of MCAo (A) and sham (B) brain tissue 24 hours post-injury. Each template consisted of 39 lanes of 4-7 antibody probes each. The far right lane contains molecular weight markers for reference. The named protein spots were either increased or decreased relative to sham animals.

Figure 4A:
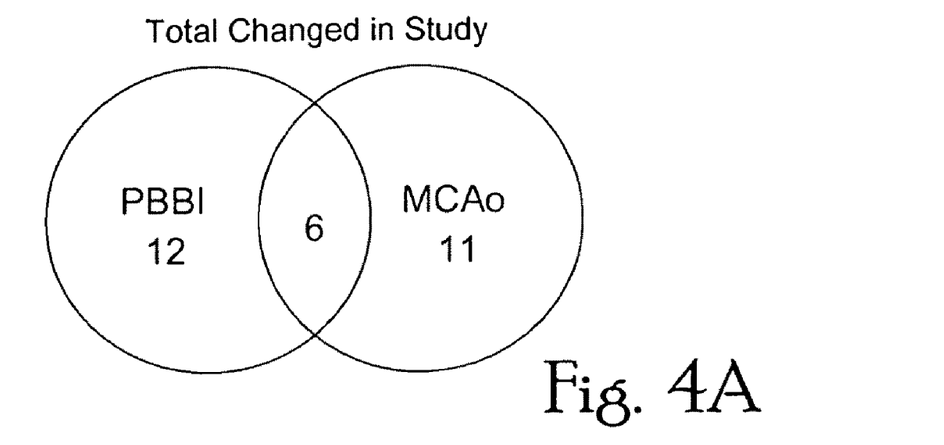
FIGS. 4a-4c: are diagrams showing comparison of the number of proteins exhibiting changes in abundance level from brain tissue of PBBI and MCAo injured rats as indicated by high throughput immunoblotting (HTPI)
Figure 4B:
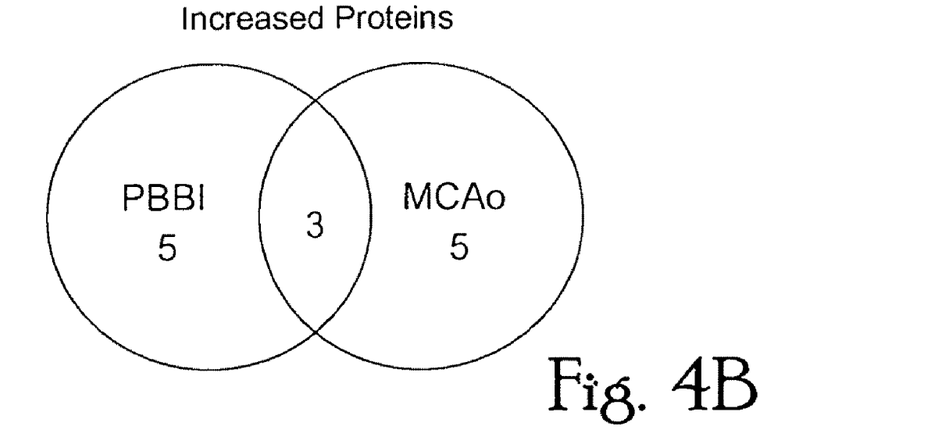
Figure 4C:
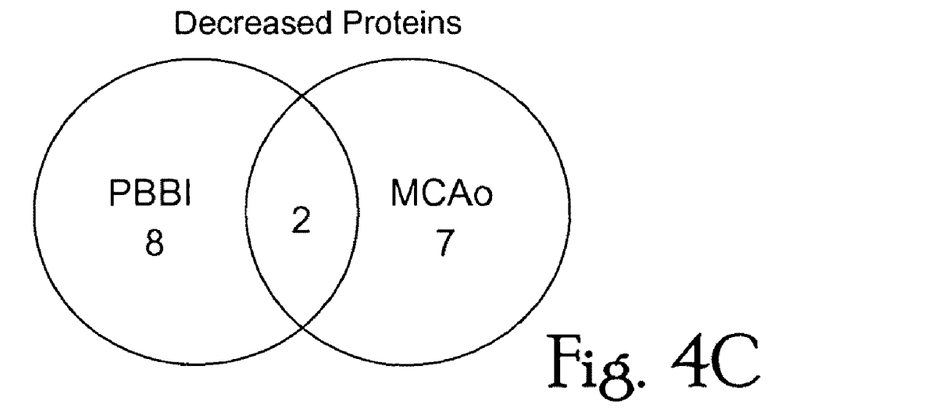

FIGS. 4a-4c: Comparison of the number of proteins exhibiting changes in abundance level from brain tissue of PBBI and MCAo injured rats as indicated by high throughput immunoblotting (HTPI). A total of 29 proteins out of 998 indicated an altered abundance level at 24 hours post-injury (FIG. 4a). The majority of protein changes were detectable in only one brain injury model as being either increased (FIG. 4b) or decreased (FIG. 4c) as compared to sham controls. Only one identified protein, p43/EMAP-II, was differentially expressed between the two models.

FIGS. 5a and 5b: Western Blot analysis (WB) was performed to verify changes for selected proteins in both blood (plasma) and brain (FIG. 5a). Quantitative measurement of WB density confirmed changes in plasma protein expression (FIG. 5b, n=3-6/group). Values are mean+/−S.D.*P<0.05 as compared to corresponding matched sham control (Student's t-test).

Figure 6:
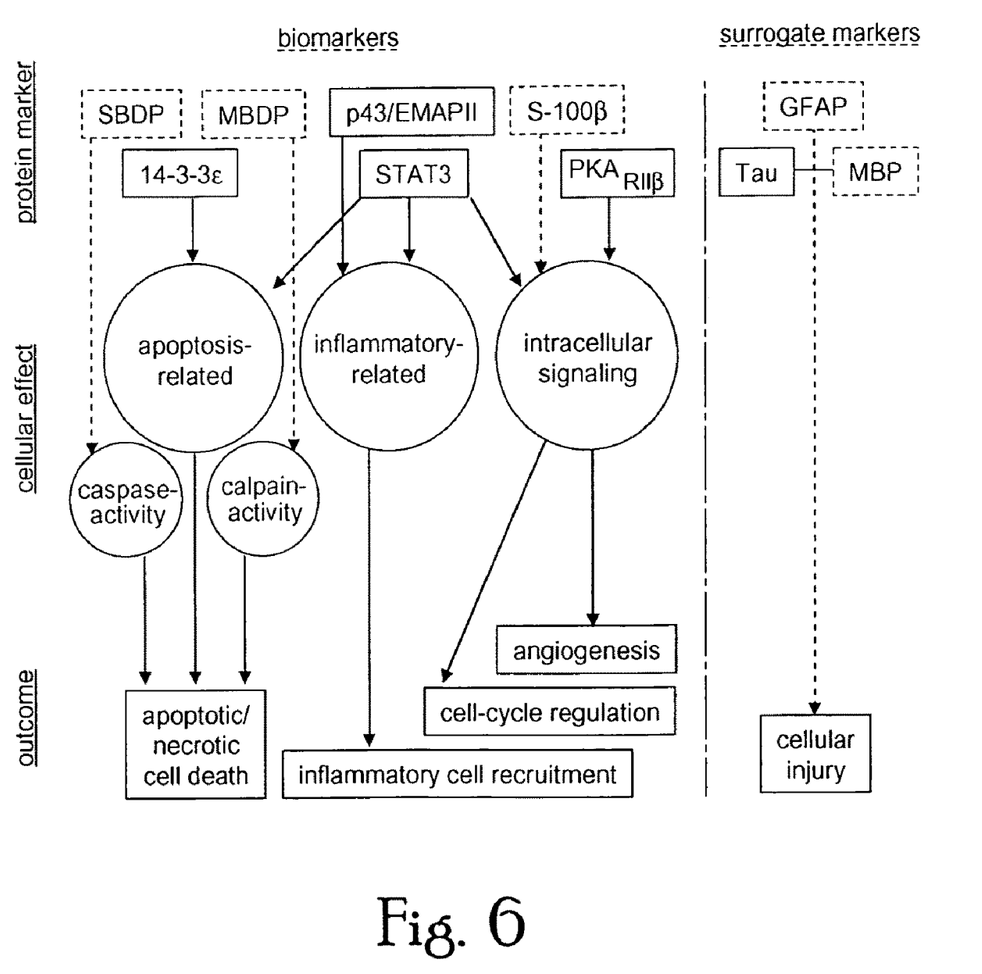
FIG. 6 is a diagram showing relevance of changes in expression of each of the five confirmed proteins detectable in blood of PBBI or MCAo injured rats.

FIG. 6: Potential relevance of changes in expression of each of the five confirmed proteins detectable in blood of PBBI or MCAo injured rats (i.e. STAT3, Tau, 14-3-3H p43/EMAP-II, and PKA$_{RIIE}$) with injury-related mechanisms of apoptosis, neuroinflammation, and intracellular signaling.

Utilization of this type of information in combination with other known protein markers (i.e. spectrin break-down products (SBDP), S-100E, myelin break down products (MBDP), myelin basic protein (MBP), and glial acidic fibrillary protein (GFAP)) could have mechanistic (i.e. biomarkers) or pathological (i.e. surrogate markers) relevance to the differential diagnosis/prognosis and treatment of brain-injured patients.

Figure 7:
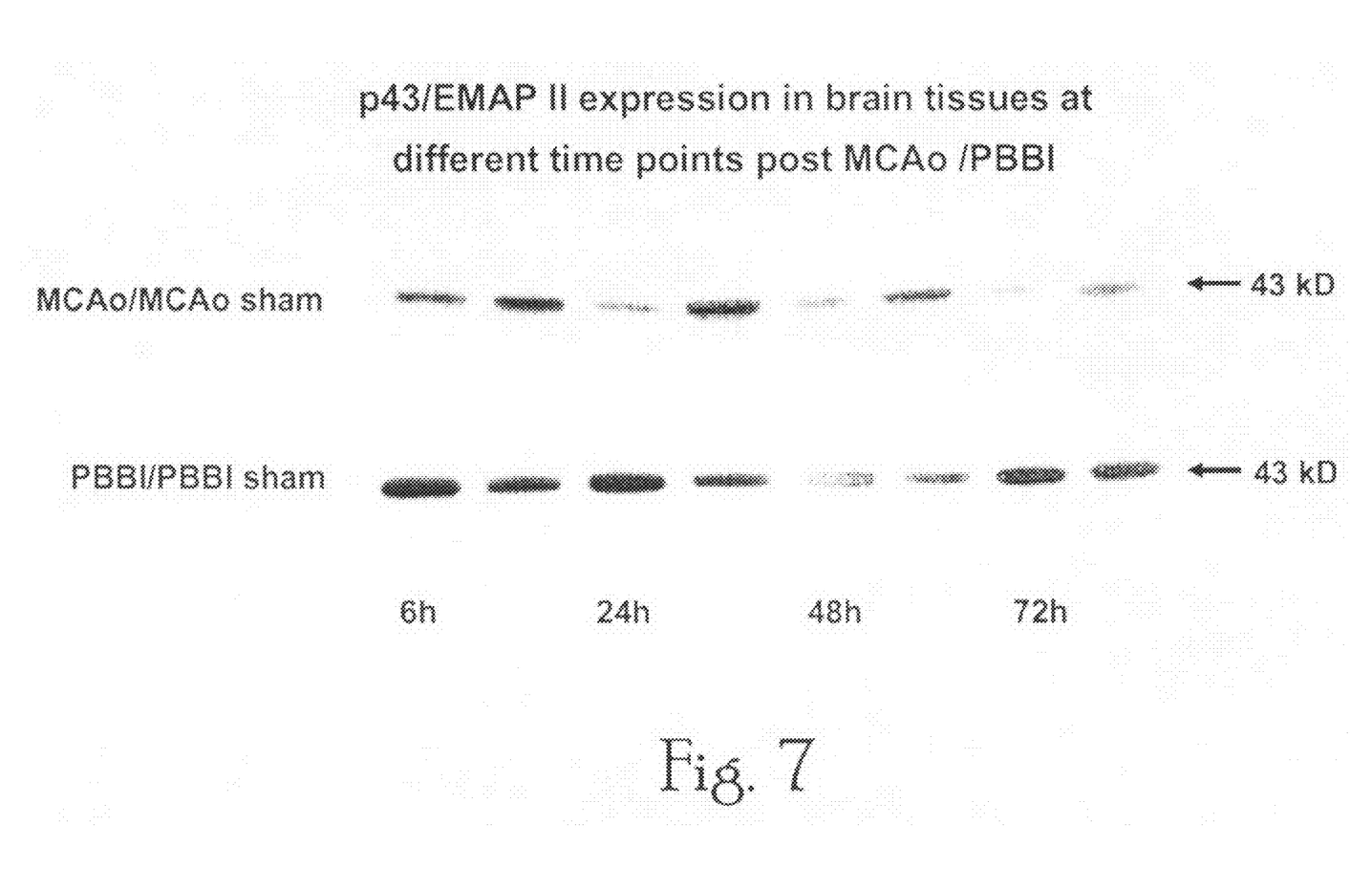
FIG. 7 is a digital image of Western Blotting results for p43/EMAP-II protein expression in brain tissues at different time points following MCAo/PBBI.

FIG. 7: Digital image of preliminary Western Blotting results indicating the time course expression profile of p43/EMAP-II in rat brain at different time points post MCAo/PBBI. Blots are to be read from left to right in pairs. For MCAo/MCAo sham, it can be seen in each of the pairs, the p43/EMAP-II expression in MCAo is less than the sham at each of 6 h, 24 h, 48 h and 72 hours. For PBBI/PBBI sham, it can be seen in each of the pairs, the p43/EMAP-II expression in PBBI is greater than the sham at each of 6 h, 24 h, 48 h and 72 hours.

Figure 8:
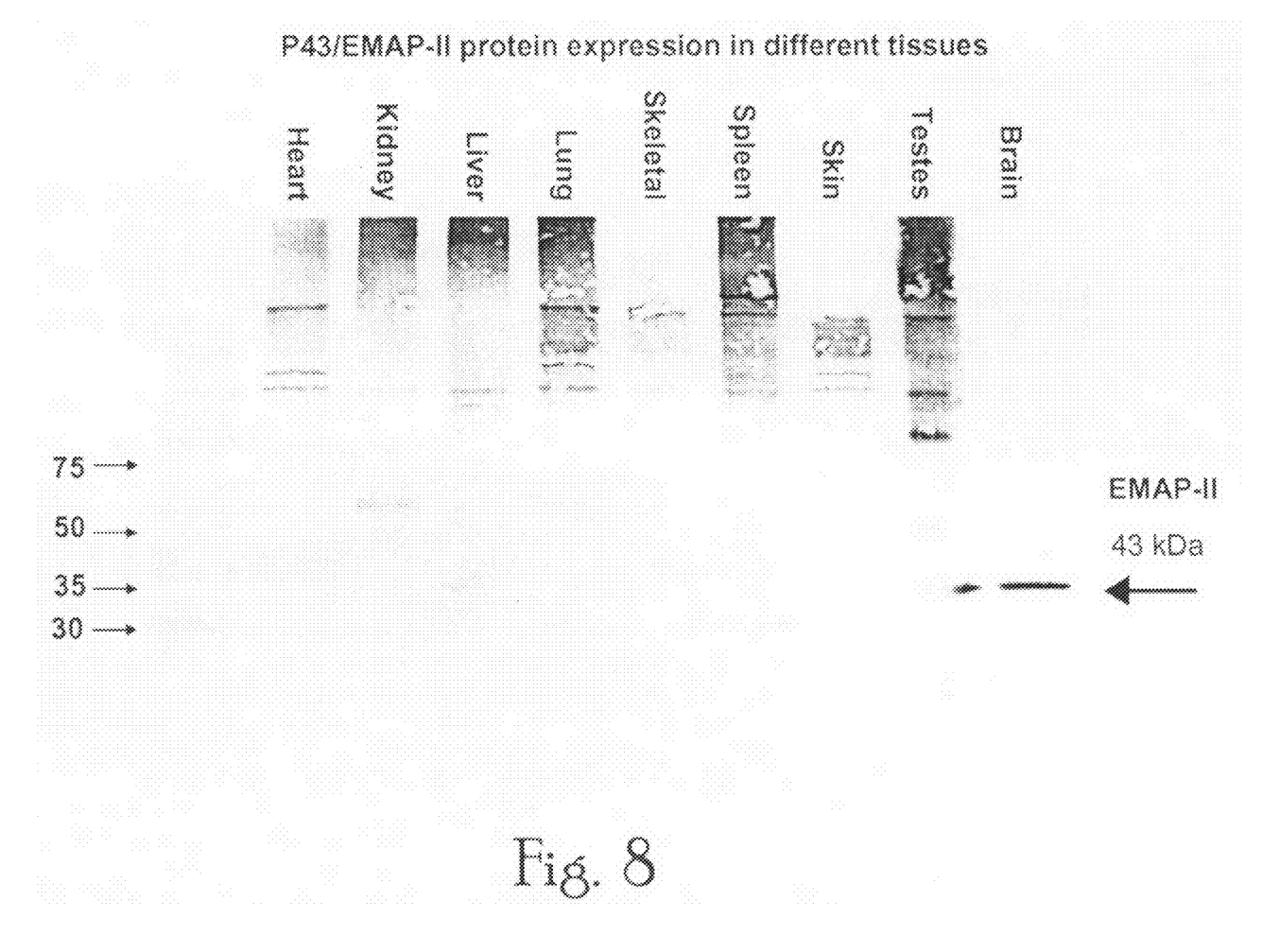
FIG. 8 is a digital image of Western Blotting results for p43/EMAP-II protein expression in different types of tissue.

FIG. 8: Digital image of Western Blots indicating p43/EMAP-II protein expression in different types of tissues. It can be seen that EMAP-II is primarily expressed in brain tissue with minimal expression in other types of tissue such as testes.

FIG. 9: Conceptual drawing of a rat brain showing method for inducing MCAo.

FIG. 10: Conceptual drawing of a rat brain showing method used for inducing PBBI.

Human Data:

Using sandwich ELISA specific to human EMAP-II, CSF (20 μL) and serum (50 μL) samples from a human traumatic brain injury patient (at different post-injury time points) and pooled uninjured controls were analyzed. It was found that EMAP-II levels were elevated in CSF (a) and serum (b) in human TBI samples, when compared to human controls. Table 3 shows the results. In addition, EMAPII levels in pooled CSF and serum samples from TBI patients at some time points were also elevated when compared to those in pooled uninjured controls.

TABLE 3

| Human CSF samples | [EMAPII] ng/mL |
|---|---|
| (a) | |
| pooled Control | 0.000 |
| pooled TBI/0 h | 0.000 |
| pooled TBI/24 h | 0.000 |
| pooled TBI/48 h | 0.000 |
| pooled TBI/72 hr | 0.306 |
| pooled TBI/96 hr | 0.000 |
| #16/0 hr | 0.334 |
| #16/12 h | 1.077 |
| #16/24 h | 1.471 |
| #16/48 h | 0.687 |
| #16/72 h | 0.509 |

TABLE 3-continued

| Human CSF samples | [EMAPII] ng/mL |
|---|---|
| #16/120 h | 0.008 |
| #16/168 h | 0.000 |
| #34/24 h | 0.300 |
| #34/48 h | 0.000 |
| #34/72 h | 0.002 |
| #34/168 h | 0.000 |

(b)

| | |
|---|---|
| pooled Control | 0.059 |
| pooled TBI/0 h | 0.133 |
| pooled TBI/48 h | 0.043 |
| pooled TBI/72 hr | 0.163 |
| pooled TBI/96 h | 0.000 |
| #16/0 h | 0.902 |
| #16/12 h | 0.160 |
| #16/120 h | 0.178 |
| #16/72 h | 0.064 |
| #16/168 h | 0.240 |
| #34/0 h | 0.045 |
| #34/12 hr | 0.204 |

REFERENCES

Berti R, Williams A J, Moffett J R, Hale S L, Velarde L C, Elliott P J, Yao C, Dave J R, Tortella F C (2002) Quantitative real-time RT-PCR analysis of inflammatory gene expression associated with ischemia-reperfusion brain injury. *J Cereb Blood Flow Metab* 22(9): 1068-79

Budillon A, Cereseto A, Kondrashin A, Nesterova M, Merlo G, Clair T, Cho-Chung Y S (1995) Point mutation of the autophosphorylation site or in the nuclear location signal causes protein kinase A RII beta regulatory subunit to lose its ability to revert transformed fibroblasts. *Proc Natl Acad Sci USA* 92(23):10634-8

Chen R W, Chuang D M (1999) Long term lithium treatment suppresses p53 and Bax expression but increases Bcl-2 expression A prominent role in neuroprotection against excitotoxicity. *J Biol Chem* 274(10):6039-42

Choi J S, Kim S Y, Cha J H, Choi Y S, Sung K W, Oh S T, Kim O N, Chung J W, Chun M H, Lee S B, Lee M Y (2003) Upregulation of gp130 and STAT3 activation in the rat hippocampus following transient forebrain ischemia. *Glia* 41(3):237-46

Conklin D S, Galaktionov K, Beach D (1995) 14-3-3 proteins associate with cdc25 phosphatases. *Proc Natl Acad Sci USA* 92:7892-96

Daemen M A, van't Veer C, Denecker G, Heemskerk V H, Wolfs T G, Clauss M, Vandenabeele P, Buurman W A (1999) Inhibition of apoptosis induced by ischemia-reperfusion prevents inflammation. *J Clin Invest* 104(5):541-9

Dave J R, Yao C. Moffett J R, Berti R. Koenig M, Tortella F C (2003) Down regulation of sodium channel Na(v)1.1 expression by veratridine and its reversal by a novel sodium channel blocker, RS100642, in primary neuronal cultures. *Neurotox Res* 5(3):213-20

Funahashi M (2003) Effects of ischemic preconditioning on myocardial protective on cardiac surgery: possibility of ischemic preconditioning and adenosine administration. *Ann Thorac Cardiovasc Surg* 9(5):307-13

Gabbita S P, Scheff S W, Menard R M, Roberts K, Fugaccia I, Zemlan F P (2005) Cleaved-tau: a biomarker of neuronal damage after traumatic brain injury. *J Neurotrauma* 22(1): 83-94

Hartings J A, Rolli M L, Lu X C, Tortella F C (2003) Delayed secondary phase of peri-infarct depolarizations after focal cerebral ischemia: relation to infarct growth and neuroprotection. *J Neurosci* 23(37): 11602-10

Hu S, Loo J A, Wong D T (2003) Human body fluid proteome analysis. *Proteomics* 6:6326-53

Ingebrigtsen T, Romner B (2002) Biochemical serum markers of traumatic brain injury. *J Trauma* 52:798-808

Irazuzta J E, de Courten-Myers G, Zemlan F P, Bekkedal M Y, Rossi J 3rd (2001) Serum cleaved Tau protein and neurobehavioral battery of tests as markers of brain injury in experimental bacterial meningitis. *Brain Res* 913(1):95-105.

Kobeissy F H, Ottens A K, Zhang Z Q, Dave, J R, Tortella F C, Hayes R L, Wang K K W (2006) Differential proteomic analysis of traumatic brain injury biomarker study using CAX-PAGE/RPLC-MSMS method. *Mo Cell Proteomics* 5:1887-98

Lee N, Neitzel K L, Di Marco A, Laufer R, MacLennan A J (2005) Penetrating brain injury leads to activation of ciliary neurotrophic factor receptors. *Neurosci Lett* 374(3):161-5

Li H C, Zhang G Y (2003) Activation of STAT3 induced by cerebral ischemia in rat hippocampus and its possible mechanisms. *Sheng Li Xue Bao* 55(3):311-6

Li Y, Rubin C S (1995) Mutagenesis of the regulatory subunit (RII beta) of cAMP-dependent protein kinase II beta reveals hydrophobic amino acids that are essential for RII beta dimerization and/or anchoring RII beta to the cytoskeleton. *J Biol Chem* 270(4): 1935-44

Liu M C, Akle V, Zheng W, Dave J R, Tortella F C, Hayes R L, Wang K K (2006a) Comparing calpain- and caspase-3-degradation patterns in traumatic brain injury by differential proteome analysis. *Biochem J* 394:715-25

Liu M C, Akle V, Zheng W, Kitlen J, O'steen B, Lamer S F, Dave J R, Tortella F C, Hayes R L, Wang K K (2006b) Extensive degradation of myelin basic protein isoforms by calpain following traumatic brain injury. *J Neurochem* 98(3):700-12

Lu X C, Williams A J, Yao C, Berti R, Hartings J A, Whipple R, Vahey M T, Polavarapu R G, Woller K L, Tortella F C, Dave J R (2004) Microarray analysis of acute and delayed gene expression profile in rats after focal ischemic brain injury and reperfusion. *J Neurosci Res* 77(6):843-57

Lu X C, Williams A J, Tortella F C (2001) Quantitative electroencephalography spectral analysis and topographic mapping in a rat model of middle cerebral artery occlusion. *Neuropathol Appl Neurobiol* 27(6):481-95

Mechoulam H, Pierce E A (2005) Expression and Activation of STAT3 in Ischemia-Induced Retinopathy. *Invest Ophthalmol Vis Sci* 46(12):4409-16

Mueller C A, Schluesener H J, Conrad S, Meyermann R, Schwab J M (2003) Lesional Expression of a pro-inflammatory and antiangiogenic cytokine EMAP-II confined to endothelium and microglia/macropahges during secondary damage following experimental traumatic brain injury. *J Neuroimmunol* 135:1-9

Mueller C A, Schluesener, H J, Conrad S, Meyermann R, Schwab J M (2003) Spinal cord injury induces lesional expression of the proinflammatory and antiangiogenic cytokine EMAP-II. *J Neurotrauma* 20(10):1007-1015

Moshang E, Ling G, Groer J (2003) A model of penetrating traumatic brain injury using an air inflation technique. National Technical information service, DAMD 17-01-1-0742, 5285 Port Royal Rd, Springfield, Va. 22161.

Ottens A K, Kobeissy F H, Wolper R A, Haskins W E, Hayes R L, Denslow N D, Wang K K W (2005) A multidimensional differential proteomic platform using dual phase ion-exchange chromatography-polyacrylamide gel electrophoresis/reverse phase liquid chromatography tandem mass spectrometry. *Anal Chem* 77(15):4836-45

Quevillon S, Aquo F, Robinson J C, Mirande M (1997) The p43 component of the mammalian multi-synthetase complex is likely to be the precursor of the endothelial monocyte-activating polypeptide II cytokine. *J Biol Chem* 272 (51):32573-9

Saito A, Narasimhan P, Hayashi T, Okuno, S, Ferrand-Drake M, Chan P H (2004) Neuroprotective role of a proline-rich Akt substrate in apoptotic neuronal cell death after stroke: relationships with nerve growth factor. *J Neurosci* 24(7): 1584-93

Schluesener, H. J., Seid, K., Zhao, Y., Meyermann, R., 1997. Localization of endothelialmonocyte-activating polypeptide II (EMAP-II), a novel proinflammatory cytokine, to lesions of experimental autoimmune encephalomyelitis, neuritis and uveitis: expression by monocytes and activated microglial cells. Glia. 20, 365-372.

Siman R, Zhang C, Roberts V L, Pitts-Kiefer A, Neumar R W (2005) Novel surrogate markers for acute brain damage: cerebrospinal fluid levels correlate with severity of ischemic neurodegeneration in the rat. *J Cereb Blood Flow Metab* 25(11): 1433-44

Tortella F C, Britton P, Williams A, Lu X C, Newman A H (1999) Neuroprotection (focal ischemia) and neurotoxicity (electroencephalographic) studies in rats with AHN649, a 3-amino analog of dextromethorphan and low-affinity N-methyl-D-aspartate antagonist. *J Pharmacol Exp Ther* 291(1):399-408

Tsuruta F, Sunayama J, Mori Y, Hattori S, Shimizu S, Tsujimoto Y, Yoshioka K, Masuyama N, Gotoh Y (2004) JNK promotes Bax translocation through phosphorylation of 14-3-3 proteins. *EMBO J* 23:1889-99

Williams A, Hartings J, Lu X, Rolli M and Tortella F (2006) Experimental penetrating ballistic brain injury: differential time courses of cell death, axonal degeneration, hemorrhage, and inflammation. *J Neurotrauma* 23(12):1828-46

Williams A, Ling G, Tortella F (2006) Severity level and injury track determine outcome following a penetrating ballistic-like brain injury (PBBI) in the rat *Neurosci Lett* 408:183-8

Williams A J, Berti R, Dave J R, Elliot P J, Adams J, Tortella F C (2004) Delayed treatment of ischemia/reperfusion brain injury: extended therapeutic window with the proteosome inhibitor MLN519. *Stroke* 35:1186-91

Williams A J, Hartings J A, Lu X C, Rolli M L, Dave J R, Tortella F C (2005) Characterization of a new rat model of penetrating ballistic brain injury. *J Neurotrauma* 22(2): 313-31

Yao C, Williams A J, Cui P, Berti R, Hunter J C, Tortella F C, Dave J R (2002) Differential pattern of expression of voltage-gated sodium channel genes following ischemic brain injury in rats. *Neurotox Res* 4(1):67-75

Yao C, Williams A J. Hartings J A, Lu X C, Tortella F C, Dave J R (2005) Down-regulation of the sodium channel Na(v) 1.1 alpha-subunit following focal ischemic brain injury in rats: in situ hybridization and immunohistochemical analysis. *Life Sci* 77(10):1116-29

What is claimed is:

1. A method of diagnosing ischemic brain injury comprising:
    a) obtaining a cerebral spinal fluid, blood serum, blood plasma or brain tissue sample from a patient suspected of having brain injury;
    b) measuring a level of endothelial monocyte-activating polypeptide II (EMAP II) and/or p43/endothelial monocyte-activating polypeptide II (p43/EMAP II) in said sample;
    c) comparing said level to EMAP II and/or p43/EMAP II in a control sample, said control sample obtained from a patient that has no brain injury, wherein if there is a decrease in the level of EMAP II relative to the control, there is ischemic brain injury.

2. The method of claim 1, wherein the decrease in EMAP II and/or p43/EMAP II is 2.1 to 2.3 fold relative to the normal control for ischemic brain injury.

3. The method of claim 1, wherein said steps of obtaining and measuring of said levels of EMAP II and/or p43/EMAP II are conducted at between 6 and 48 hours after injury or suspected injury.

* * * * *

UNITED STATES PATENT AND TRADEMARK OFFICE
CERTIFICATE OF CORRECTION

PATENT NO.        : 7,799,536 B2                                  Page 1 of 1
APPLICATION NO.   : 12/290174
DATED             : September 21, 2010
INVENTOR(S)       : Dave et al.

It is certified that error appears in the above-identified patent and that said Letters Patent is hereby corrected as shown below:

On the Title page, Item (75)
The inventor's name Xi-Chun May should be spelled Xi-Chun May Lu.

Signed and Sealed this

Twenty-third Day of November, 2010

David J. Kappos
*Director of the United States Patent and Trademark Office*